US00PP15837P2

(12) United States Plant Patent
Westhoff

(10) Patent No.: US PP15,837 P2
(45) Date of Patent: Jul. 5, 2005

(54) ***CALIBRACHOA* PLANT NAMED 'WESCASUNO'**

(50) Latin Name: ***Calibrachoa* sp.**
Varietal Denomination: Wescasuno

(75) Inventor: Heinrich Westhoff, Südlohn (DE)

(73) Assignee: Josef und Heinrich Westhoff Gartenbau-Spezialkulturen, Südlohn (DE)

( * ) Notice: Subject to any disclaimer, the term of this patent is extended or adjusted under 35 U.S.C. 154(b) by 0 days.

(21) Appl. No.: 10/919,006

(22) Filed: Aug. 16, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

PP12,756 P2 * 7/2002 Westhoff ..... Plt./263
PP13,976 P2 * 7/2003 Kievit ..... Plt./263
PP14,779 P2 * 5/2004 Bessho ..... Plt./263

OTHER PUBLICATIONS

UPOV ROM GTITM Computer Database, GTI Jouve Retrieval Software 2004/04 Citation for Wescasuno.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Calibrachoa* plant named 'Wescasuno', characterized by its cascading and uniform growth habit; freely branching habit and short internodes; dense and bushy plant habit; medium-sized leaves; medium-sized flowers; and numerous golden yellow-colored flowers.

1 Drawing Sheet

Botanical designation: *Calibrachoa* sp.
Variety denomination: 'Wescasuno'.

BACKGROUND OF THE INVENTION

The present Invention relates to a new and distinct cultivar of *Calibrachoa* plant, botanically known as *Calibrachoa* sp., and hereinafter referred to by the cultivar name 'Wescasuno'.

The new *Calibrachoa* is a product of a planned breeding program conducted by the Inventor in Südlohn, Germany. The new *Calibrachoa* originated from a cross-pollination made by the Inventor of a proprietary selection of *Calibrachoa* identified as code number 01P407, not patented, as the female, or seed, parent with a proprietary selection of *Calibrachoa* identified as code number 01P107, not patented, as the male, or pollen, parent. The new *Calibrachoa* was discovered and selected by the Inventor in 2001 in a controlled environment in Südlohn, Germany as a single plant within the resulting progeny from the cross-pollination.

Asexual reproduction of the new cultivar by terminal cuttings at Südlohn, Germany since 2002, has shown that the unique features of this new *Calibrachoa* are stable and reproduced true to type in successive generations.

SUMMARY OF THE INVENTION

Plants of the cultivar Wescasuno have not been observed under all possible environmental conditions. The phenotype may vary with variations in environment such as temperature, light intensity and daylength without, however, any variance in genotype.

The following traits have been repeatedly observed and are determined to be the unique characteristics of 'Wescasuno'. These characteristics in combination distinguish 'Wescasuno' as a new and distinct cultivar:

1. Cascading and uniform growth habit.
2. Freely branching habit and short internodes, dense and bushy plant habit.
3. Medium-sized leaves.
4. Medium-sized flowers.
5. Numerous golden yellow-colored flowers.

Plants of the cultivar Wescasuno can be compared to plants of the female parent selection. In side-by-side comparisons conducted in Südlohn, Germany, plants of the new *Calibrachoa* differed from plants of the female parent selection in the following characteristics:

1. Plants of the new *Calibrachoa* had smaller flowers than plants of the female parent selection.
2. Plants of the new *Calibrachoa* and the female parent selection differed in flower color as plants of the female parent selection had lighter yellow-colored flowers.

Plants of the cultivar Wescasuno can be compared to plants of the male parent selection. In side-by-side comparisons conducted in Südlohn, Germany, plants of the new *Calibrachoa* differed from plants of the male parent selection in the following characteristics:

1. Plants of the new *Calibrachoa* had smaller leaves than plants of the male parent selection.
2. Plants of the new *Calibrachoa* had narrower stems than plants of the male parent selection.
3. Plants of the new *Calibrachoa* and the male parent selection differed in flower color.

Plants of the new *Calibrachoa* can also be compared to plants of the *Calibrachoa* cultivar Wescasun, disclosed in U.S. Plant Pat. No. 12,756. In side-by-side comparisons conducted in Südlohn, Germany, plants of the new *Calibrachoa* differed from plants of the cultivar Wescasun in the following characteristics:

1. Plants of the new *Calibrachoa* had stronger stems than plants of the cultivar Wescasun.
2. Plants of the new *Calibrachoa* had smaller leaves than plants of the cultivar Wescasun.

3. Plants of the new *Calibrachoa* had smaller flowers than plants of the cultivar Wescasun.
4. Plants of the new *Calibrachoa* and the cultivar Wescasun differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Calibrachoa.*

The photograph at the top of the sheet comprises a side perspective view of typical flowering plants of 'Wescasuno' grown in a container.

The photograph at the bottom of the sheet is a close-up view of a typical flower and leaves of 'Wescasuno'.

DETAILED BOTANICAL DESCRIPTION

Plants used in the aforementioned photographs and for the following description were grown under conditions which closely approximate commercial production conditions during the spring and summer in a glass-covered greenhouse in Südlohn, Germany. Plants were about 20 weeks from planting rooted cuttings and grown in containers. During the production of the plants, the day temperatures ranged from 20 to 25° C., night temperatures ranged from 16 to 18° C. and light levels ranged from 3,000 to 50,000 lux.

In the following description, color references are made to The Royal Horticultural Society Colour Chart, 2001 Edition, except where general terms of ordinary dictionary significance are used.

Botanical classification: *Calibrachoa* sp. cultivar Wescasuno.

Parentage:

*Female parent.*—Proprietary selection of *Calibrachoa* sp. identified as 01P407, not patented.

*Male parent.*—Proprietary selection of *Calibrachoa* sp. identified as 01P107, not patented.

Propagation:

*Type cutting.*—Terminal vegetative cuttings.

*Time to initiate roots.*—About 18 to 20 days at 20° C.

*Time to develop roots.*—About 20 to 28 days at 20° C.

*Root description.*—Numerous, fine, fibrous, and well-branched.

Plant description:

*Form.*—Annual flowering plant; cascading; uniform, rounded appearance, plants eventually become spherical in overall shape. Freely branching with lateral branches forming at every node. Vigorous growth habit.

*Usage.*—Appropriate for hanging baskets, window boxes and patio containers.

*Plant height* (*from soil level to top of plant plane*).—About 18 to 29 cm.

*Plant length* (*from soil level to lateral branches apices*).—About 80 cm.

*Plant diameter* (*area of spread*).—About 60 cm.

*Stem description.*—Main branches, length: About 65 cm. Main branches, diameter: About 2.5 mm. Lateral branches, length: About 30 to 36 cm. Lateral branches, diameter: About 1.3 mm. Internode length: About 1.2 cm. Texture: Pubescent. Strength: Strong, wiry. Color: 144B.

*Foliage description.*—Arrangement: Alternate; simple; sessile. Length: About 3.6 cm. Width: About 1 cm. Shape: Oblanceolate. Apex: Acute. Base: Attenuate. Margin: Entire. Aspect: Mostly flat. Texture, upper and lower surfaces: Sparsely pubescent. Venation: Pinnate. Color: Developing foliage, upper surface: 146A to 146B. Developing foliage, lower surface: 146B. Fully expanded foliage, upper surface: 137A; midvein, 137B. Fully expanded foliage, lower surface: 137C; midvein, 137D.

Flower description:

*Flower type and habit.*—Medium-sized flowers; flowers face upright or outward; single, axillary. Flowers not persistent. Freely flowering with flowers forming at every axil.

*Natural flowering season.*—Spring until frost in the autumn; flowering continuous.

*Flowering longevity on the plant.*—About one week.

*Flower size.*—Diameter: About 3 cm. Depth (height): About 2.1 cm. Tube length: About 1.4 cm. Throat diameter, distal end: About 1 cm. Tube diameter, proximal end: About 3 mm.

*Flower buds.*—Length: About 1.4 cm. Diameter: About 4 mm. Shape: Oblong. Color: Towards the base, 1C; mid-section, 1C, venation, 166A; towards the apex, 35C, venation, 166A.

*Corolla.*—Arrangement/appearance: Single whorl of five petals, fused into flared trumpet. Petal length from throat: About 1.2 cm. Petal width: About 1.4 cm. Petal shape: Roughly spatulate with rounded to slightly acute apex. Petal margin: Entire. Petal texture, upper and lower surfaces: Smooth, satiny. Color: Petal, when opening, upper surface: 12A. Petal, when opening, lower surface: 12C to 12D. Petal, fully opened, upper surface: 12A to 12C; venation, 165A to 165B overlain with 185A. Petal, fully opened, lower surface: 12D; venation, 165A. Flower throat (inside): 12A; venation, 166A. Flower tube (outside): 12C; venation, 187A.

*Sepals.*—Arrangement/appearance: Single whorl of five sepals, star-shaped. Length: About 1.3 cm. Width: About 3.3 mm. Shape: Lanceolate. Apex: Acute. Margin: Entire. Texture, upper and lower surfaces: Pubescent. Color, upper surface: 137B to 137C. Color, lower surface: 138A.

*Peduncles.*—Length: About 2.1 cm. Width: About 0.9 mm. Strength: Flexible, wiry. Texture: Slightly pubescent. Color: 144A.

*Reproductive organs.*—Stamens: Quanity per flower: Five. Anther shape: Four-parted, ovate. Anther length: About 1.2 mm. Anther diameter: About 1.1 mm. Filament length: About 8 mm. Filament color: 145C. Anther color: 12B. Pollen amount: Moderate. Pollen color: 12A. Pistils: Quantity per flower: One. Pistil length: About 1.1 cm. Stigma shape: Ovate. Stigma color: 143A. Style length: About 7 mm. Style color: 145B. Ovary color: 145B.

*Seed/fruit.*—Seed and fruit production has not been observed.

Disease/pest resistance: Plants of the new *Calibrachoa* have not been noted to be resistant to pathogens and pests common to *Calibrachoa.*

Temperature tolerance: Plants of the new *Calibrachoa* have been observed to be tolerant to temperatures ranging from 2 to 30° C.

It is claimed:

1. A new and distinct cultivar of *Calibrachoa* plant named 'Wescasuno', as illustrated and described.

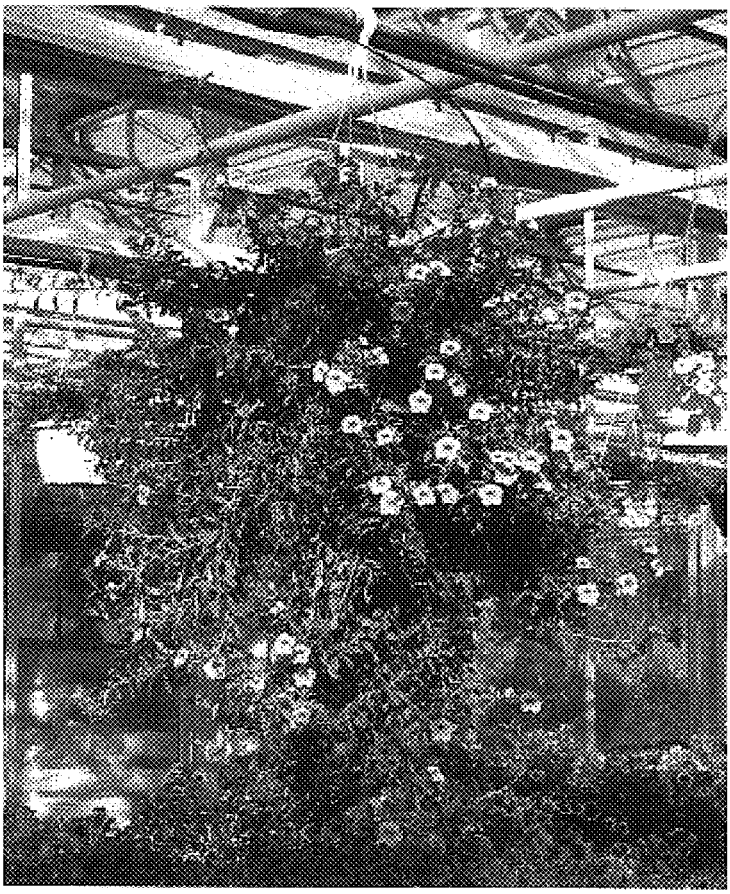
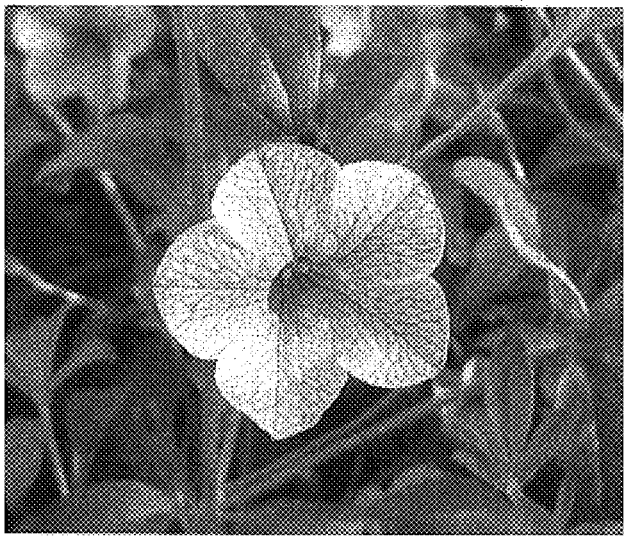

* * * * *